Dec. 31, 1968 J. D. LISSEMORE Plant Pat. 2,854
ROSE PLANT
Filed July 27, 1967
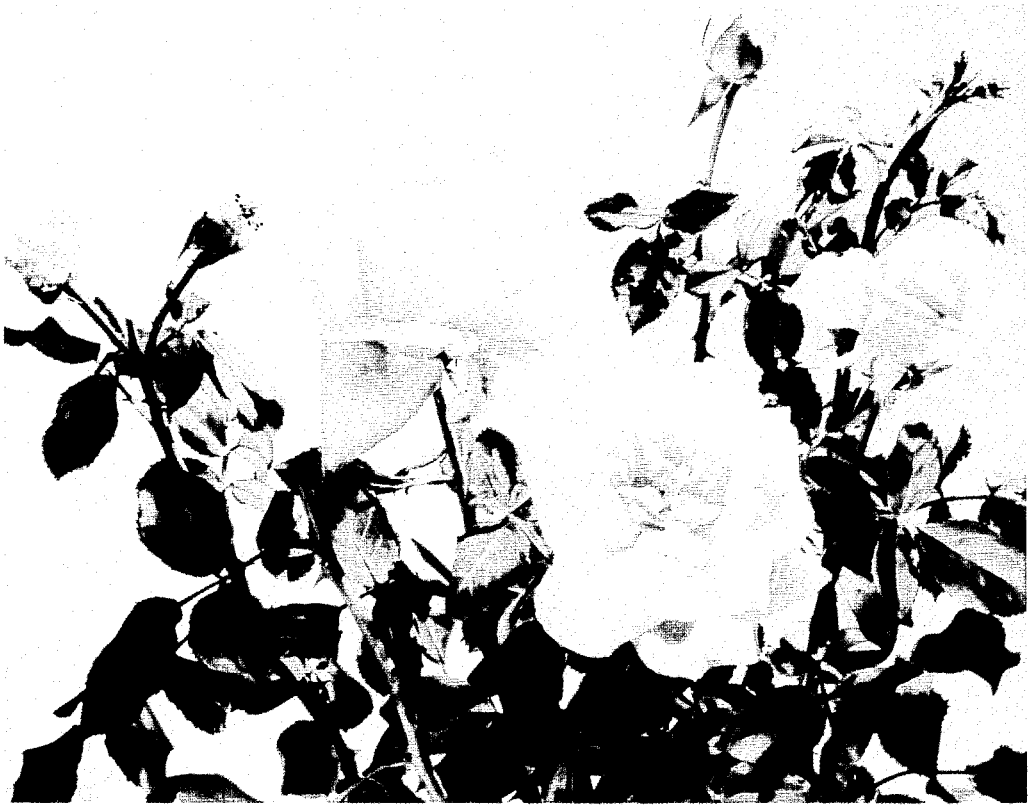
JACK D. LISSEMORE
INVENTOR
By
Brown, Dome, Benedict, Sweeney & Mathis
Attorneys United States Patent Office Plant Pat. 2,854
Patented Dec. 31, 1968

2,854
ROSE PLANT

Jack D. Lissemore, Tenafly, N.J., assignor to The Conard-Pyle Company, West Grove, Pa., a corporation of Pennsylvania Filed July 27, 1967, Ser. No. 656,604
1 Claim. (Cl. Plt.—5)

ABSTRACT OF THE DISCLOSURE

A new and distinct variety of climbing shrub rose plant originated by crossing "New Dawn" with "Spartan."

*Description of the invention*

This invention relates to a new and distinct variety of rose plant of the hardy climbing shrub type which was originated by me by crossing "New Dawn" with "Spartan."

The primary objective of this breeding was to create a distinct variety of rose different from all other known varieties of roses in several important characteristics.

This new variety differs from its seed parent, "New Dawn," by having blooms of a carmen rose color much deeper than the pink of "New Dawn" and with more petals. Plant growth is less vigorous than "New Dawn" and leaves are larger, with a darker color.

This new variety differs from its pollen parent, "Spartan," by having vigor and growth characteristics of a climber or large shrub rather than a floribunda. The flower color is lighter than "Spartan," with larger size and not so perfectly formed.

Asexual reproduction of my new variety by budding was performed in West Grove, Pa.

The accompanying drawing shows typical specimens of the flowers and foliage of my new variety in different stages of development and as depicted in color as nearly true as is reasonably possible to make the same in a color illustration of this character.

The following is a detailed description of my new variety with color terminology in accordance with the horticultural color chart of the Royal Horticultural Society.

Type: Hardy; climbing shrub, outdoor; seedling; garden decoration.
Class: Climber.
Propagation: It does hold its distinguishing characteristics through succeeding propagations by budding.

*The flower*

Locality where grown: West Grove. Pa.
Flowers borne: Singly, sometimes four-five to stem; in irregular rounded cluster; normal, medium stems.
Quantity of bloom: Free outdoors.
Continuity: Intermittent.
Fragrance: Slight, centifolia.
Bud:
*Peduncle*—Medium; slender; medium erect; medium reddish green; almost rough; few; hairs; red glandular tipped.
*Before calyx breaks.*—Size: Small. Form: short globular; without appendages; with slender medium bristle-like parts equal to ¼ of its length.
*As calyx breaks.*—Color: Crimson 22/1.
*As first petal opens.*— Size: Medium. Form: short ovoid, Color: Outside.—Crimson 22/2 with pod green 061/1 at very base of petal. Inside: Camellia Rose 622 fading to crimson 22/2 at petal edges mid vein of pod green 061/1 extending from lower quarter of petal to base.
*Opening.*—It does open up well.

Bloom:
Size when fully open: Medium, 2½ inches to 3½ inches.
Petalage: Double; from 40 to 50 petals; arranged regularly.
Form: High centered at first; becoming flat; petals remaining at first loosely rolled outward; becoming later at maturity tightly flat.
Petals: Medium leathery; with inside velvety; outside velvety.
Shape: Outer.—obovate; with 1 notch sometimes. Intermediate.—almost round; with 1 tooth. Inner—almost round; no notches.

This description of a newly opened flower was made from a rose grown outdoors in September 1966 at West Grove, Pa.

Color.—Outer petal: Outside surface—Crimson 22/2; inside surface—Neyron rose 623/1 with pod green 061/1 at base. Intermediate petal: Outside surface—Crimson 22/2 with rose madder 23/2 over lower third of petal; inside surface—Carmine rose 621/2 with rose madder 23/2 over lower ⅓ of petal. Pod green 061/1 at point of attachment. Inner petal: Outside surface: Carmine rose 621/1. Pod green 061/1 at point of attachment; inside surface: Carmine rose 621. Pod green 061/1 at point of attachment.

This description was made from a rose that was open for three days, outdoors in September 1966, at West Grove, Pa.

Color.—Outer petal: Outside surface—Crimson 22/2 with Rose Madder 23/2 over basal ⅓. Pod Green 061/1 at basal point of attachment. Inside surface—Rose Madder 23/2 with Neyron Rose 623/1 over basal ⅓. Pod green 061/1 at basal point of attachment. Inner petal: Outside surface—Neyron Rose 623/1. Inside surface—Camellia Rose 622/1.
*General color effect.*—Newly opened flower; Carmine Rose 621/3 through 621/1 at bloom center. Three days open: Camellia Rose 622/1.
*Behavior.*—Drop off cleanly.
*Flower longevity.*—On bush in garden five days in September, cut roses grown outdoors kept at living room temperatures four days in September.

*Reproductive organs*

Stamens: Many; regularly arranged pistils mixed with few petaloids.
Filaments: Many, with anthers; medium.
*Color.*—Canary 2/2.
Anthers: Open at various times; medium.
*Color.*—Buttercup Yellow 5.
Seldom anther fused with a petaloid.
Pollen: Sparse; gold.
Pistils: Medium.
Styles: Uneven; medium; thin; loosely bunched.
Stigma: White yellow.
Ovaries: All enclosed in receptacle.
Hips: None observed.
Sepals: Permanent; medium; spear shaped slightly recurved.
Seeds: None observed.

*Plant*

Foliage:
*Leaves.*—Seven; abundant; medium; moderately glossy.
*Leaflets.*—Shape: Oval with apex acute; base acute; margin simply serrate. Color: Mature—upper surface: Spinach Green 0960. Maroon (general color term) at notch tips; under surface: Willow Green 000862/1. Young—upper surface: Willow Green 000862 with maroon (general term) around margin; under surface: Spinach green 0862/3 with maroon (general color term) toward outer margins.

*Rachis.*—Medium. Upper side: Hairy. Under side: Moderately smooth.

*Stipules.*—Medium; long; medium wide; short points; turning out at an angle of more than 45°; with glandular tipped hairs.

*Disease.*—Resistance comparable to the average variety growing under the same cultural conditions.

Growth:

*Habit.*—Bushy climbing much branched.

*Growth.*—Vigorous.

*Canes.*—Medium.

*Main stems.*—Dull. Color: Scheeles Green 860/1. Prickles: Several. Color: Maroon (general color term). Hairs: None.

*Branches.*—Dull. Color: Scheeles green 860/3.

Prickles: Several. Color: Maroon (general color term). Hairs: None.

New shoots: Bright. Color: Fern green 0862/3. Prickles: Several. Color: Fern green 0862/3 with maroon (general color term) toward base. Hairs: Few. Color: Greenish-white (general color term).

I claim:

1. A new and distinct variety of rose plant of the climber class, substantially as herein shown and described, characterized particularly as to novelty by the unique combination of vigorous well branched growth, bloom of large size and fully petalled with carmine rose color occurring abundantly in June and intermittently through the growing season mostly singly on lateral branches, and in clusters at the tip of main branches which are well covered with glossy foliage.

No references cited.

ROBERT E. BAGWILLER, *Primary Examiner.*